US00PP32576P2

(12) United States Plant Patent
Cain

(10) Patent No.: US PP32,576 P2
(45) Date of Patent: Dec. 8, 2020

(54) SWEET CHERRY TREE NAMED 'IFG CHER-TEN'

(50) Latin Name: *Prunus avium*
Varietal Denomination: IFG Cher-ten

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 16/873,384

(22) Filed: Apr. 6, 2020

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./180, 181
See application file for complete search history.

*Primary Examiner* — Susan McCormick Ewoldt

(57) ABSTRACT

This invention is a new and distinct sweet cherry variety denominated 'IFG Cher-ten'. The new sweet cherry tree is characterized by producing large size, dark red fruits having reniform shape. Fruits ripen early, are firm with medium acidity and have a good cherry flavor. Fruit stems are long, medium thick, have strong attachment and stay green during storage and shipping. 'IFG Cher-ten' is self-incompatible having S1S3 pollen alleles. The tree has a medium-low chilling requirement of about 400 to 500 hours. It produces very few doubled and spurred fruits in high summer temperature regions.

1 Drawing Sheet

Latin name of the genus and species claimed: *Prunus avium.*

Variety denomination: 'IFG Cher-ten'.

BACKGROUND OF THE INVENTION

The new and distinct cherry described and claimed herein originated from open pollinated seeds of fruits of the unnamed IFG selection 01C041-021-090 growing near Delano, in Kern County, Calif. collected in May 2007. The male parent is unknown. The seeds were stratified, germinated and the resulting 204 seedlings were planted in the field near Delano, Kern County, Calif. in April 2008. The present variety of sweet cherry tree was selected as a single plant in May 2013 and was first asexually propagated in December 2014 by grafting onto *Prunus avium* rootstock. This propagule was found to reproduce true-to-type by asexual propagation. All propagation was done near Delano, Kern County Calif.

BRIEF SUMMARY OF THE INVENTION

The new sweet cherry tree 'IFG Cher-ten' is characterized by producing large size, dark red fruits having reniform shape. Fruits ripen early, are firm with medium acidity and have a good cherry flavor. Fruit stems are long, medium thick, have strong attachment and stay green during storage and shipping. 'IFG Cher-ten' is self-incompatible having S1S3 pollen alleles. The tree has a medium-low chilling requirement of about 400 to 500 hours. It produces very few doubled and spurred fruits in high summer temperature regions such as the Southern San Joaquin Valley of California.

In comparison to the 'Brooks' (U.S. Plant Pat. No. 6,676), which is a major variety grown in warm regions, the present variety ripens with to slightly earlier, has fewer undesirable doubled and spurred fruits, has better firmness, darker flesh and skin color, and has superior stem attachment and storage characteristics. "IFG Cher-ten' has a lower chilling requirement than 'Brooks' and can be successfully grown in lower chill regions where 'Brooks' cannot be grown.

In comparison to 'IFG Cher-three' (U.S. Plant Pat. No. 30,011), the present variety has a slightly higher chilling requirement, ripens slightly later, and has larger fruit size. 'IFG Cher-ten' exhibits less pebbling of the skin surface and better stem quality during long term storage as compared to 'IFG Cher-three'. 'IFG Cher-ten' is in the S1S3 pollen incompatibility group as opposed to 'IFG Cher-three' which is S3S6.

In comparison to its female parent, IFG selection 01C041-021-090, the present variety ripens slightly later, has larger fruits, and better storage ability. IFG selection 01C041-021-090 also differs in its pollen compatibility group being S3S4 rather than S1S3 of 'IFG Cher-ten'.

BRIEF DESCRIPTION OF THE DRAWING

The accompanying photographic drawing illustrates in full color 'IFG Cher-ten', taken from a 10-year old tree. The photograph was taken outdoors with indirect lighting. The colors are as nearly true as is reasonably possible in a color representation of this type.

An actively growing shoot tip can be seen in the upper portion of the drawing.

Typical mature fruit, fruit in cross section and cleaned and dried fruit pits are displayed in the lower half of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2015 by The Royal Horticultural Society, London, England.

Throughout this specification subjective description values conform to those set forth by the International Board for Plant Genetic Resources (IBPGR) 'Cherry Descriptor List' (*Prunus* spp.) (1985) which was developed with full support from the Commission of the European Communities (CEC) Programme Committee for Plant Disease Resistance Breeding and the Use of Genebanks.

The descriptive matter which follows pertains to 'IFG Cher-ten' plants grown in the vicinity of Delano, Kern County, Calif. during 2016 and 2017, and is believed to apply to plants of the variety grown under similar conditions of soil and climate elsewhere:

Tree:

*General*.—Age — 10 yrs. old. Height — About 2.6 M when pruned. Width — About 3.2 M when pruned. Vigor — Vigorous. Density of foliage — Dense. Form — Spreading. Root stock — *Prunus mahaleb*. Resistance/susceptibility to typical pests and diseases of *Prunus avium* species — not observed to date. Chilling requirements — Medium low, slightly lower than 'Brooks'. Graft compatibility — Good: produces compatible graft unions with *Prunus avium*, 'Mazzard' seedling (non-patented), and *Prunus mahaleb* seedlings (non-patented).

*Trunk*.—Trunk diameter of 10-year old trees, 30 cm above the soil line — About 22.0 cm. Lenticel size — Medium. Lenticel dimensions — Length: About 1.9 cm. Width: About 0.4 cm. Lenticel shape — Elliptical shape oriented horizontally. Lenticel color — Grey: 201A. Trunk surface texture — Moderately rough. Outer bark color — The following colors were observed: Grey: 201A and 201B.

Branches:

1-*year old wood*.—Vertical top growth length — Long: About 70.9 cm. Horizontal Growth Length — Medium: About 42.1 cm. Diameter — Vertical growth: About 0.8 cm. Horizontal growth: About 0.8 cm. Internode length — About 4.3 cm. Number of lenticels — Few: About 3 lenticels per linear cm. Lenticel size — Small. Lenticel dimensions — Length: About 0.1 cm. Width: About 0.1 cm. Lenticel shape — Round. Bark color — The following colors were observed: Greyed-orange: 175A and 175B.

2-*year old wood*.—Length — About 29.1 cm. Diameter — About 1.1 cm. Internode length — About 3.8 cm. Number of lenticels — Few: About 3 to 4. Lenticel dimensions — Length: About 0.3 cm. Width: About 0.1 cm. Lenticel shape — Elliptical shape oriented horizontally. Bark color — The following colors were observed: Grey: 201B and Greyed-orange: 166B and 177B.

Buds:

*Vegetative buds*.—Shape — Elongated. Vegetative bud dimensions — Length: About 1.8 cm. Width: About 0.4 cm. Bud burst — Feb. 9, 2017.

*Flower buds*.—Flower bud dimensions — Length: About 1.4 cm. Width: About 0.5 cm. Shape — Oval. Placement — At bud positions mostly 1 to 6 on first year wood. Average number of flower buds on first year wood: 4. Number of flower buds per spur on second year wood — 2 to 4. Average — 3. Color — The following colors were observed: Greyed-orange: 175A and 175B.

Leaves:

*Mature leaves*.—Leaf dimensions — Length: About 15.2 cm. Width: About 6.7 cm. Leaf shape — Ovate: symmetric on both sides of central axis. Shape of tip — Acuminate: narrowly. Shape of base — Rounded. Margin — Serrated: regular: pointed. Leaf profile — Involute. Venation — Arcuate. Vein color — The following colors were observed: Yellow-green: N144C and 145A.

*Upper surface*.—Upper surface pubescence — None. Upper leaf surface color — Yellow-green: 147A. Surface texture — Smooth.

*Lower surface*.—Lower surface pubescence — Sparse: only on veins. Lower leaf surface color — Yellow-green: 147B.

*Petiole*.—Petiole dimensions — Length: About 2.9 cm. Width: About 0.2 cm. Upper surface of petiole color — The following colors were observed: Grey-purple: 187B and Green: 144A. Lower surface of petiole color — The following colors were observed: Yellow-green: N144C and 145A. Petiole groove — Wide. Petiole pubescence — Very sparse: only on lower surface.

*Glands*.—Number of glands — 1 to 2. Gland dimensions — Length: About 0.25 cm. Width: About 0.2 cm. Gland shape — Mixture of globose and reniform. Gland location — On petiole. Gland color — Greyed-purple: 183C. Leaf stipule — Present.

Flowers:

*Blooming period*.—Early Season.

*Blooming dates*.—First Bloom: Feb. 17, 2017. Full Bloom: Mar. 5, 2017.

*Number of flowers per cluster*.—2 to 3. Average — About 2.7.

*Corolla*.—Composed of unfused petals, somewhat overlapping.

*Corolla diameter*.—About 2.8 cm.

*Petal number*.—5.

*Petal length*.—About 1.7 cm.

*Petal width*.—About 1.6 cm.

*Margin waviness*.—Weak.

*Division of upper margin*.—Notched.

*Color of petal upper surface*.—White: N155A.

*Color of petal lower surface*.—White: N155A.

*Peduncle*.—Length: About 2.3 cm. Width: About 0.17 cm.

*Peduncle color*.—Yellow-green: 144B.

*Number of sepals*.—5.

*Sepal length*.—About 0.7 cm.

*Sepal width*.—About 0.4 cm.

*Sepal shape*.—Narrow elliptic.

*Sepal color*.—Upper surface: Yellow-green: 146C. Lower surface: Greyed-orange: 176A.

*Filament*.—Length: 0.6 to 1.5 cm. Width: About 0.1 cm.

*Filament color*.—White: NN155C.

*Anther color*.—The following colors were observed: Greyed-orange: N163D and 163B.

*Pollen color*.—The following colors were observed: Greyed-orange: 163A and 163B.

*Pollen production*.—Average.

*Self-compatibility of flowers*.—Self-incompatible.

*Flower compatibility group*.—S1S3.

Fruit:

*General*.—Ripening period — Early to mid-season: Approximately: May 1, 2017. Use — Fresh market. Keeping quality — Good. % Titratable acidity — About 0.93%. Refractometer test — Soluble solids: Brix: About 19.6. Firmtech II (g/mm) — About 359. Flavor — Excellent aromatic with good sugar/acid balance. Juice color — Greyed-purple: 183A. Juice amount — Juicy. Eating quality — Excellent flavor and texture.

*Stem*.—Stem — Length: About 5.3 cm. Width: About 0.2 cm. Stem color — Yellow-green: 144A. Stem cavity — Medium. Stem retention during storage — Excellent. Stem storage quality — Moderate to good.

*Berry*.—Uniformity of size — Uniform. Shape — Reniform with somewhat pointed stylar end. Fruit Weight — About 11.1 gm. Apical Diameter — About 2.7 cm. Diameter transversely across suture — About 2.3 cm. Diameter at right angle to suture plane — About 2.9 cm. Suture — None. Percent of excessively deep or split sutures — About 0%. Doubles — About 0%.

*Skin*.—Thickness — Thick. Texture — Mostly smooth with very little indentation noted at lenticels. Skin color — The following colors were observed: Greyed-purple: 187A. Tendency to crack — Not susceptible.

*Flesh*.—Texture — Firm. Color — Greyed-purple: 184A. Stone cavity color — Greyed-purple: N186C.

*Stone*.—Shape — Oblong. Length — About 1.1 cm. Width across suture — About 1.0 cm. Width at right angle to suture plane — About 0.7 cm. Type — Semi-free. Surface texture — Slightly rough. Stone Color when dry — Orange-white: 159A. Tendency to split — None. Base — Flat. Apex — Rounded. Ventral edge — Narrow suture subtended by 2 somewhat prominent ridges converging at base and apex. Dorsal edge — Somewhat prominent ridge extending from base to apex, slight wing near base.

What is claimed:

1. A new and distinct variety of sweet cherry tree as herein illustrated and described.

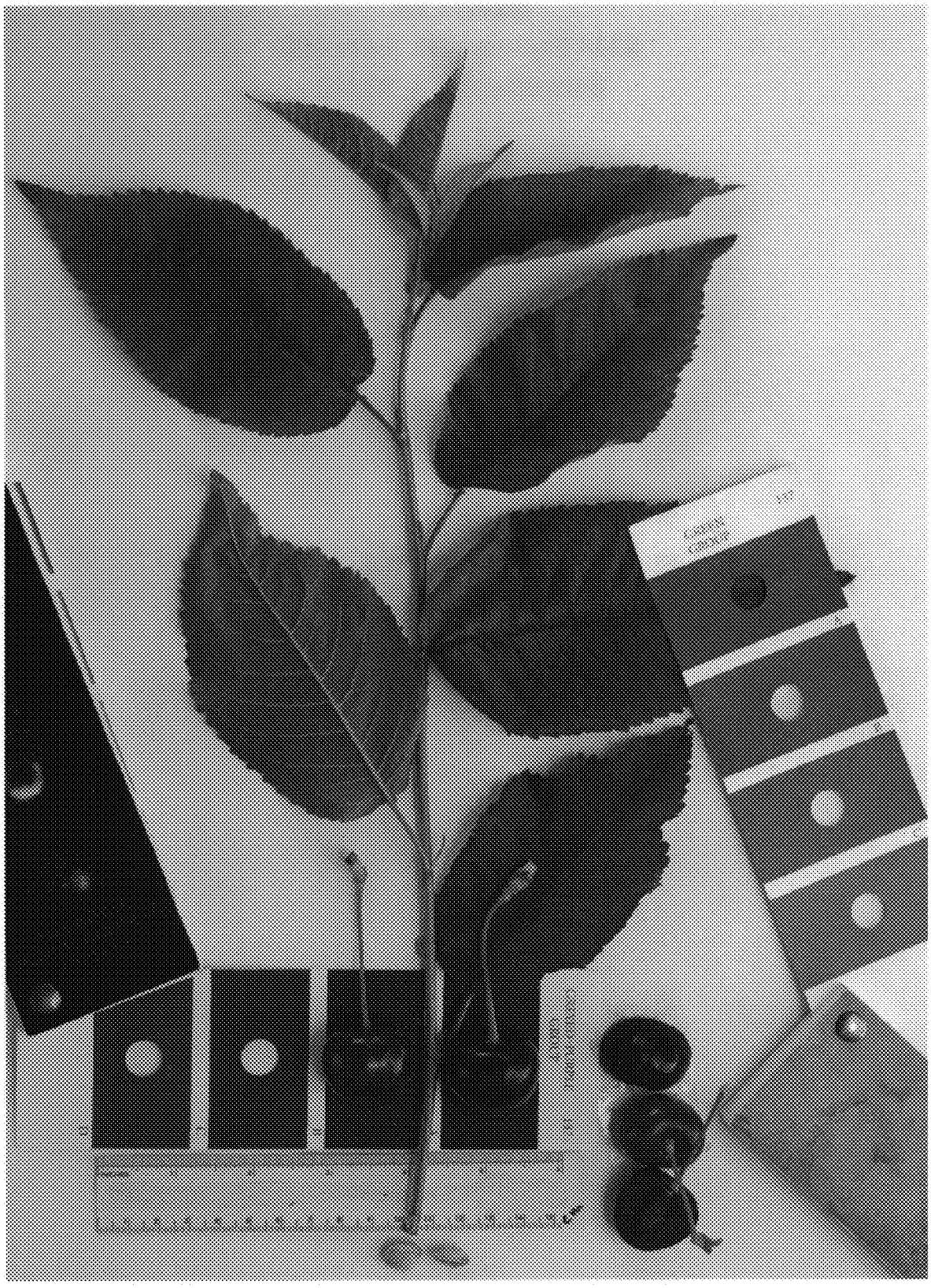

* * * * *